US009907512B2

(12) United States Patent
Kleiss et al.

(10) Patent No.: US 9,907,512 B2
(45) Date of Patent: Mar. 6, 2018

(54) SYSTEM AND METHOD FOR PROVIDING AUDITORY MESSAGES FOR PHYSIOLOGICAL MONITORING DEVICES

(71) Applicant: GENERAL ELECTRIC COMPANY, Schenectady, NY (US)

(72) Inventors: James Alan Kleiss, Oconomowoc, WI (US); Karel William Barnoski, Dublin, CA (US)

(73) Assignee: General Electric Company, Schenectady, NY (US)

( * ) Notice: Subject to any disclaimer, the term of this patent is extended or adjusted under 35 U.S.C. 154(b) by 202 days.

(21) Appl. No.: 14/564,470

(22) Filed: Dec. 9, 2014

(65) Prior Publication Data

US 2016/0157790 A1 Jun. 9, 2016

(51) Int. Cl.
*A61B 5/00* (2006.01)

(52) U.S. Cl.
CPC ............ *A61B 5/7415* (2013.01); *A61B 5/486* (2013.01); *A61B 5/7282* (2013.01); *A61B 5/746* (2013.01)

(58) Field of Classification Search
CPC ................ A61B 5/7405; A61B 5/7415; A61B 5/025055; A61B 5/74; A61B 5/741; A61B 5/0002; A61B 5/0741; A61B 5/746; A61B 5/7465; A61B 5/7475; G08B 21/18; G08B 21/182; G08B 23/00; G01H 2220/37; G01H 2220/376; G01H 2220/386; G01K 15/00; G01K 15/02; G01K 15/04; G01K 15/043; G06F 9/54; G06F 9/542; G06F 9/546; G06F 19/34; G06F 19/345
See application file for complete search history.

(56) References Cited

U.S. PATENT DOCUMENTS

| | | | |
|---|---|---|---|
| 3,868,665 A | 2/1975 | Treglown | |
| 4,576,178 A | 3/1986 | Johnson | |
| 5,438,607 A | 8/1995 | Przygoda, Jr. et al. | |
| 5,730,140 A * | 3/1998 | Fitch .................... | A61B 5/0205 600/514 |
| 6,450,172 B1 | 9/2002 | Hartlaub et al. | |
| 6,727,814 B2 | 4/2004 | Saltzstein et al. | |
| 7,138,575 B2 | 11/2006 | Childs, Jr. et al. | |
| 7,508,307 B2 | 3/2009 | Albert | |

(Continued)

OTHER PUBLICATIONS

Eve Hoggan, Roope Raisamo, and Stephen Brwester; Mapping Information to Audio and Tactile Icons; Glasgow Interactive Systems Group, University of Glasgow; Tampere Unit for Computer-Human Interaction, University of Tempere, Nov. 4, 2009.

(Continued)

*Primary Examiner* — Van Trieu

(74) *Attorney, Agent, or Firm* — Grogan, Tuccillo & Vanderleeden, LLP

(57) ABSTRACT

A system includes at least one medical device configured to generate a plurality of messages and a control unit in the at least one device. The control unit is configured to generate an auditory signal corresponding to one of the plurality of messages, wherein the auditory signal is configured based on a functional relationship linking psychological sound perceptions in a clinical environment to acoustic and musical sound properties. The functional relationship includes a plurality of types of auditory messages defining seven unique categories.

18 Claims, 6 Drawing Sheets

(56) References Cited

U.S. PATENT DOCUMENTS

| | | | |
|---|---|---|---|
| 7,742,807 B1* | 6/2010 | Walls | A61B 5/0402 600/509 |
| 8,183,451 B1 | 5/2012 | Panaiotis | |
| 9,230,419 B2* | 1/2016 | Beggs | B60Q 1/2673 |
| 2004/0121767 A1 | 6/2004 | Simpson et al. | |
| 2004/0172222 A1 | 9/2004 | Simpson et al. | |
| 2004/0263322 A1 | 12/2004 | Onaru et al. | |
| 2005/0188853 A1 | 9/2005 | Scannell, Jr. | |
| 2005/0288563 A1 | 12/2005 | Feliss et al. | |
| 2007/0116220 A1 | 5/2007 | Eckel et al. | |
| 2010/0312095 A1 | 12/2010 | Jenkins et al. | |
| 2011/0015493 A1 | 1/2011 | Koschek | |
| 2012/0123241 A1 | 5/2012 | Stilley et al. | |
| 2012/0123242 A1 | 5/2012 | Stilley et al. | |
| 2013/0035961 A1* | 2/2013 | Yegnanarayanan | G06F 19/322 705/3 |
| 2013/0297347 A1* | 11/2013 | Cardoza | G06F 19/322 705/3 |
| 2013/0297348 A1* | 11/2013 | Cardoza | G06F 19/322 705/3 |
| 2014/0111335 A1* | 4/2014 | Kleiss | G10K 15/00 340/540 |
| 2015/0164436 A1* | 6/2015 | Maron | G06F 19/327 340/540 |
| 2016/0048655 A1* | 2/2016 | Maitra | G06F 19/3456 705/3 |
| 2016/0117901 A1* | 4/2016 | Zhang | G06F 19/345 340/286.07 |
| 2016/0300019 A1* | 10/2016 | Baluta | G06F 19/322 |

OTHER PUBLICATIONS

Judy Edworthy and Neville Stanton; A user-centred approach to the design and evaluation of auditory warning signals; Department of Psychology, University of Plymouth, Mar. 27, 2007.

Ross Teague, Art Swanson; "Device Development: More than Just Hearing the Customer"; MDDI Medical Device and Diagnostic Industry News Products and Suppliers; May 1, 2006; pp. 1-3.

Bruce N. Walker, Gregory Kramer; "Mapping and Metaphors in Auditory Displays: An Experimental Assessment"; ACM Transactions on Applied Perception, vol. 2, No. 4, Oct. 2005, pp. 407-412.

* cited by examiner

| | General (e.g., high inter-cranial pressure detected) | Cardiac (e.g., systole detected) | Artificial perfusion (e.g., low cardiac output detected) | Ventilation (e.g., no breath detected) | Oxygen (e.g., pulse oximetry [SPO2] lower than 85%) | Temperature/energy delivery (e.g., temperature higher than 106 degrees) | Drug or fluid delivery (e.g., line occlusion) |
|---|---|---|---|---|---|---|---|
| High criticality patient condition | | | | | | | |
| Rare or unexpected high criticality patient condition | General | Cardiac | Artificial perfusion | Ventilation | Oxygen | Temperature/energy delivery | Drug or fluid delivery |
| Reminder high criticality alarm has been turned off | General | Cardiac | Artificial perfusion | Ventilation | Oxygen | Temperature/energy delivery | Drug or fluid delivery |
| Medium criticality patient condition | General | Cardiac | Artificial perfusion | Ventilation | Oxygen | Temperature/energy delivery | Drug or fluid delivery |
| Low-criticality patient condition | General | Cardiac | Artificial perfusion | Ventilation | Oxygen | Temperature/energy delivery | Drug or fluid delivery |
| Problem with the equipment (e.g., vent tube disconnected, loss of power, etc) | General | Cardiac | Artificial perfusion | Ventilation | Oxygen | Temperature/energy delivery | Drug or fluid delivery |
| Drug or therapy delivery has started or stopped | General | Cardiac | Artificial perfusion | Ventilation | Oxygen | Temperature/energy delivery | Drug or fluid delivery |
| A user action has been detected/received (e.g., button press) | General | Cardiac | Artificial perfusion | Ventilation | Oxygen | Temperature/energy delivery | Drug or fluid delivery |

No opinion

FIG. 4

| Cluster (# signals) | Loudness moore-glasberg (FFT) free [sone] | Loudness moore-glasberg (CPB) free [sone] | Loudness free [sone] | Loudness level free [phon] | Articulation index closed [%] | Sharpness - zwicker DIN 45631 A1 2010 free [acum] | Mean frequency kHz | Tone to noise ratio ANSI S1.13 [dB] | Tonality | Prominence ratio ANSI S1.13 [dB] | Tone level ANSI S1.13 [dB Pa] | Roughness DIN 45631 A1 2010 free [asper] | Fluctuation strength DIN 45631 A1 2010 free [vacil] |
|---|---|---|---|---|---|---|---|---|---|---|---|---|---|
| High criticality (13) | 11.96 | 12.74 | 9.48 | 72.08 | 85.29 | 1.50 | 8.94 | 6.29 | 0.37 | 20.77 | 49.85 | 1.84 | 2.55 |
| Med. criticality (5) | 7.33 | 8.01 | 5.80 | 63.47 | 91.10 | 1.80 | 8.74 | 15.45 | 0.52 | 17.19 | 42.65 | 1.05 | 2.10 |
| Low criticality (2) | 4.92 | 5.64 | 4.96 | 62.49 | 95.18 | 0.72 | 7.93 | 12.39 | 0.67 | 20.10 | 51.65 | 0.39 | 1.16 |
| Alarm reminder (1) | 11.48 | 13.36 | 10.37 | 73.41 | 83.20 | 2.92 | 11.95 | 7.31 | 0.45 | 6.76 | 50.84 | 1.56 | 3.32 |
| Equipment (3) | 6.86 | 7.60 | 6.20 | 66.16 | 95.08 | 0.94 | 8.05 | 16.23 | 0.84 | 44.64 | 47.67 | 0.43 | 1.71 |
| Timer (6) | 6.28 | 6.71 | 4.81 | 61.72 | 96.85 | 1.30 | 7.87 | 14.34 | 0.45 | 13.01 | 37.63 | 1.12 | 2.67 |
| Feedback (10) | 4.37 | 4.78 | 3.75 | 58.37 | 97.80 | 1.38 | 7.85 | 23.25 | 0.52 | 30.60 | 38.03 | 1.07 | 2.00 |

FIG. 6

SYSTEM AND METHOD FOR PROVIDING AUDITORY MESSAGES FOR PHYSIOLOGICAL MONITORING DEVICES

BACKGROUND

1. Technical Field

Embodiments of the invention relate generally to patient monitoring and, more specifically, to a system and method for providing auditory messages for physiological monitoring devices.

2. Discussion of Art

In medical environments, especially complex medical environments where multiple patients may be monitored for multiple medical conditions, standardization of alarms and/or warnings creates significant potential for confusion and inefficiency on the part of users (e.g., clinicians or patients) in responding to specific messages. For example, it is sometimes difficult for clinicians and/or users of medical devices to distinguish or quickly identify the source and condition of a particular audible alarm or warning. Accordingly, the effectiveness and efficiency with which users respond to medical messaging can be adversely affected, which, in turn, can lead to delays to responding to medical or system conditions associated with these audible alarms or warnings.

In particular, medical facilities typically include rooms that enable surgery to be performed on a patient, monitoring of a patient's medical condition, and/or patient diagnosis. At least some of these rooms include multiple medical devices that enable the clinician to perform different types of operations, monitoring, and/or diagnosis. During operation of these medical devices, at least some of the devices are configured to emit audible indications, such as audible alarms and/or warnings that are utilized to inform the clinician of a medical condition being monitored. For example, a heart monitor and a ventilator may be attached to a patient. When a medical condition arises, such as low heart rate or low respiration rate, the heart monitor or ventilator emits an audible indication that alerts and prompts the clinician to perform some action.

Under certain conditions or in certain medical environments, multiple medical devices may concurrently generate audible indications. In some instances, two different medical devices may generate the same audible indication or an indistinguishably similar audible indication. For example, the heart monitor and the ventilator may both generate a similar high-frequency sound when an urgent condition is detected with the patient, which is output as the audible indication. Therefore, under certain conditions, the clinician may not be able to distinguish whether the alarm condition is being generated by the heart monitor or the ventilator. In this case, the clinician visually observes each medical device to determine which medical device is generating the audible indication. Moreover, when three, four, or more medical devices are being utilized, it is often difficult for the clinician to easily determine which medical device is currently generating the audible indication. Thus, delay in taking action could potentially result from the inability to distinguish the audible indications from the different devices. Additionally, in some instances the clinician may not be able to associate the audible indication with a specific condition and accordingly may need to visually view the medical device to assess a course of action.

As a result, in typical clinical settings, there is a lack of inherent meaning of medical messages in the auditory environment. Accordingly, the meanings need to be learned, which can result in the lack of a timely response, particularly with a novice clinical user, potentially causing adverse consequences to patients. There is also a lack of a meaningful relationship between the physical properties of auditory device signals and the intended messages, which can result in a lack of perceptual discrimination among various auditory signals.

BRIEF DESCRIPTION

In an embodiment, a system is provided. The system includes at least one device configured to generate a plurality of messages and a control unit in the at least one medical device. The control unit is configured to generate an auditory signal corresponding to one of the plurality of messages, wherein the auditory signal is configured based on a functional relationship linking psychological sound perceptions in a clinical environment to acoustic and musical sound properties. The functional relationship includes a plurality of types of auditory messages defining seven unique categories.

In an embodiment, a method for providing auditory messages for a physiological monitoring device is provided. The method includes the steps of defining a plurality of auditory states representing a plurality of different medical messages or conditions, detecting one or more medical evens and correlating the medical event to one of the medical messages or conditions, and generating an auditory message corresponding to the detected medical event, and outputting audibly the auditory message corresponding to the detected medical event. The auditory message is configured based on a functional relationship linking psychological sound perceptions in a clinical environment to acoustic and musical sound variables, and the functional relationship includes a plurality of types of auditory messages defining seven unique categories.

In an embodiment, a system is provided. The system includes a device configured to monitor at least one physiological parameter of a patient, a control unit, and a database associated with the control unit. The database includes a classification structure for auditory medical messages, wherein the classification structure includes seven categories of auditory medical messages. Upon detection of a physiological patient parameter having a value exceeding a threshold value, the control unit is configured to select an auditory signal from one of the seven categories and audibly output the auditory signal.

DRAWINGS

The present invention will be better understood from reading the following description of non-limiting embodiments, with reference to the attached drawings, wherein below:

FIG. 4 is an exemplary data sheet utilized in connection with the method of FIG. 3.

FIG. 6 is a table showing mean values for various sound metrics of the auditory device signals and medical messages generated by the present invention.

DETAILED DESCRIPTION

Figure 1:
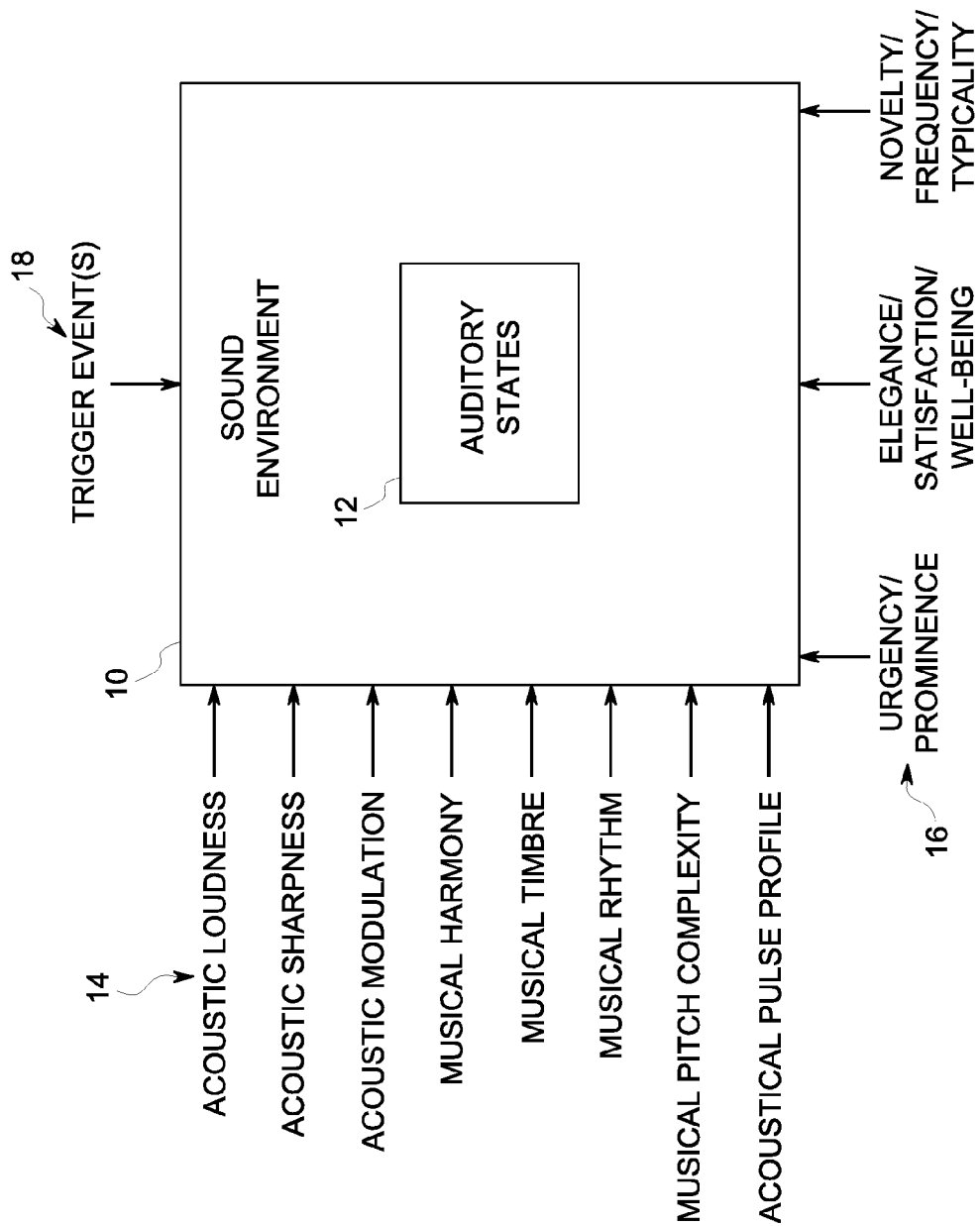
FIG. 1 is a block diagram illustrating a sounds environment in accordance with various embodiments.

Reference will be made below in detail to exemplary embodiments of the invention, examples of which are illustrated in the accompanying drawings. Wherever possible, the same reference characters used throughout the drawings refer to the same or like parts. The figures illustrate diagrams of the functional blocks of various embodiments. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

Various embodiments provide methods and systems for providing audible or auditory indications or messages, particularly audible alarms and warnings for devices, especially medical devices. The various embodiments provide methods and systems for the management of an auditory messaging environment in clinical settings. For example, a classification system may be provided, as well as a semantic mapping for these audible indications or messages to manage the perceptual discrimination among various auditory signals.

As described in more detail herein, the various embodiments provide for the differentiation of audible notifications or messages, such as alarms or warnings based on acoustical and/or musical properties. It should be noted that although the various embodiments are described in connection with medical systems having particular medical devices, the various embodiments may be implemented in connection with medical systems having different devices or non-medical systems. The various embodiments may be implemented generally in any environment or in any application to distinguish between different audible indications or messages associated or corresponding to a particular event or condition for a device or process.

As used herein, an audible or auditory indication or message refers to any sound that may be generated and emitted by a machine or device. For example, audible indications or alarms may include auditory alarms or warnings that are specified in terms of frequency, duration and/or volume of sound.

In particular, various embodiments allow for management of an auditory messaging environment, such as in a clinical setting. In one embodiment, a sound environment 10 (e.g., in a hospital room) may be provided as shown in FIG. 1. For example, the sound environment 10 may be a continuous sound environment in a clinical setting that incorporates multiple auditory states 12 representing different medical messages and/or conditions from one or more medical devices. In one embodiment, the sound environment 10 may be defined or described by various levels corresponding to different sound metric descriptors 14. For example, the sound metric descriptors may include, but are not limited to, acoustic Loudness, acoustic Sharpness, acoustic modulation (e.g., present or absent in 20 Hz to 200 Hz range), musical harmony (harmonious vs. discordant), musical timbre (natural/classical vs. artificial/mechanical), musical rhythm (complex/rhythmic vs. simple/irregular), musical pitch complexity (constant pitch vs. variable pitch), and/or acoustical pulse profile. It should be appreciated that the sound environment may be a continuous sound environment wherein one state is designated as a continuously playing background with other states representing different medical auditory messages. However, in other embodiments, a continuously playing background is not provided.

In an embodiment, the sound environment 10 also may be defined or described by one or more psychological descriptors 16. For example, the psychological descriptors 16 may include, but are not limited to, urgency/prominence, elegance/satisfaction/well-being, and/or novelty/frequency/typicality.

In accordance with various embodiments, a functional relationship is defined that links psychological sound perceptions in clinical environments to acoustic and musical sound variable (metrics and settings) to manage the sound environment 10. For example, in the illustrated embodiment, one or more trigger events 18, such as detected medical events (e.g., detected patient condition by a monitoring device) trigger specific different medical auditory messages in the sound environment 10 that are defined or designated based on one or more of the sound metric descriptors 24 and one or more of the psychological descriptors 16. Additionally, in some embodiments, the continuous sound environment parameters may be adjusted, such as based on the trigger event(s) 18, to represent different auditory messages and/or conditions. The defined auditory signals may be stored, for example, in a database that is accessible, with a particular auditory signal selected or generation and outputting based on the trigger event(s) 18.

Figure 2:
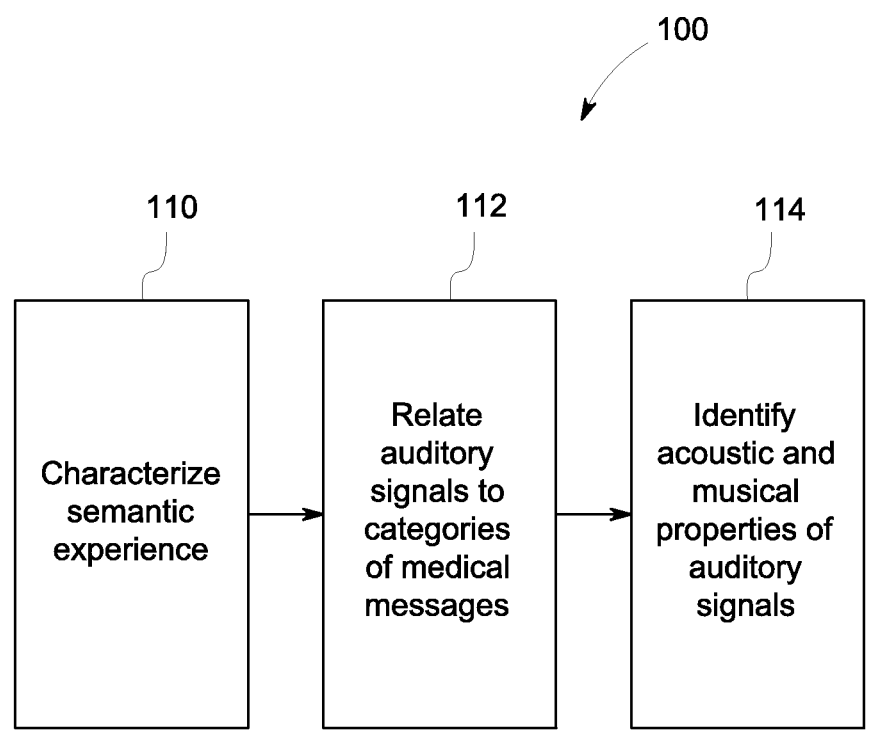
FIG. 2 is a block diagram of an exemplary auditory device signal and/or medical message process flow in accordance with various embodiments.

In various embodiments, one or more auditory device signals and/or medical messages are generated based on a common semantic experience, for example, by quantifying a nurses' semantic experience of auditory device signals. Using correlated acoustic and musical properties of auditory signals to semantic experiences provides design guidance as described in more detail herein. One embodiment of an auditory device signal and/or medical message process or design flow diagram 100 is illustrated in FIG. 2. In the illustrated embodiment, the process 100 includes characterizing a semantic experience of auditory device signals and/or medical messages at 110. For example, nurses' semantic experience of auditory device signals and/or medical messages are characterized, which in one embodiment includes using only auditory signals. The flow process 100 also includes at 112 relating the auditory signals and/or medical messages based upon a common semantic experience, such as determined from the characterization at 110. The flow process 100 additionally includes identifying acoustic and musical properties of auditory signals at 114 that are correlated with the dimensions of the semantic experience. The steps of the flow process 100 are described in more detail herein.

Figure 3:
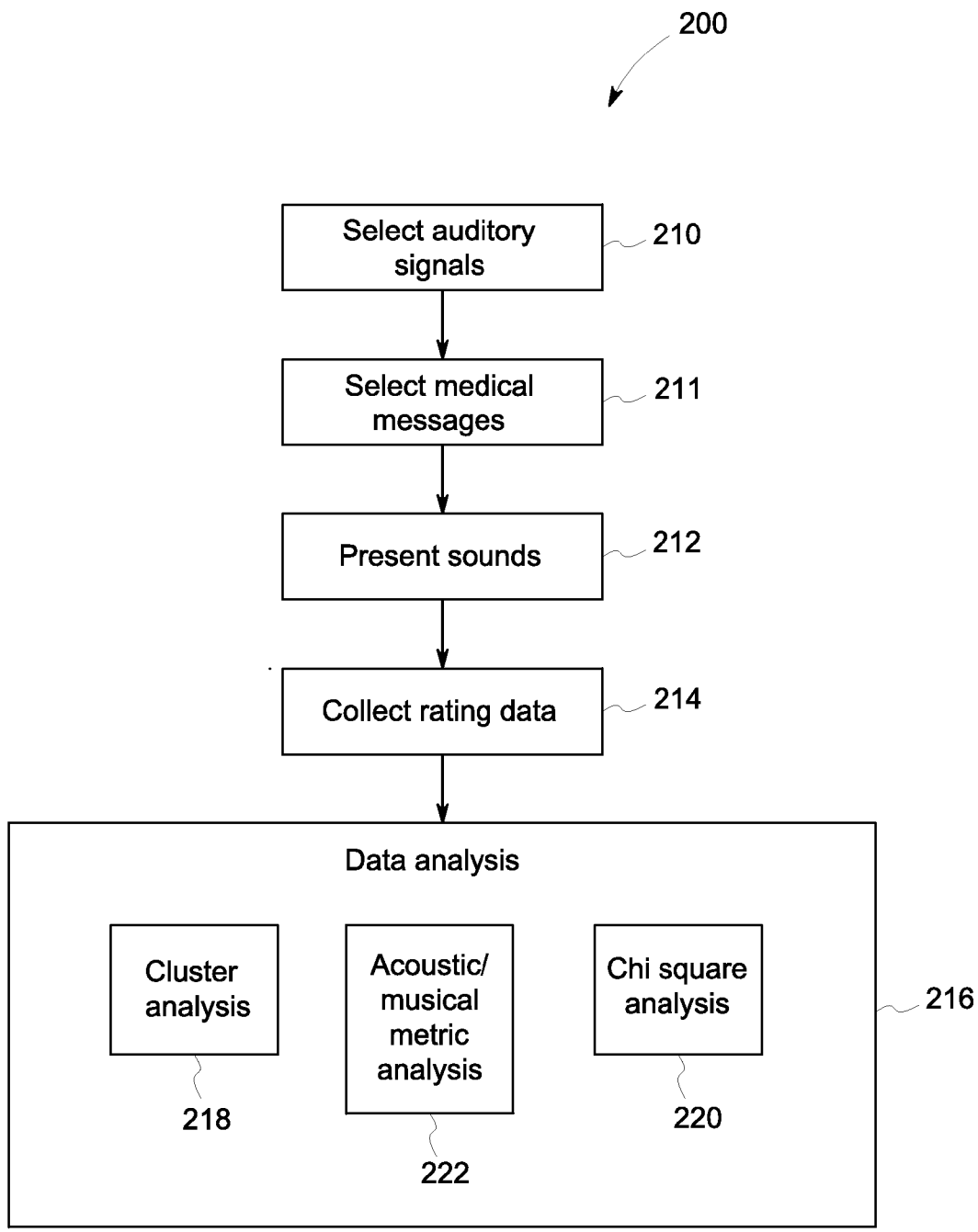
FIG. 3 is a flowchart of a method for use in generating auditory device signals and/or medical messages in accordance with various embodiments.

A method 200 for use in generating auditory device signals and/or medical messages is shown in FIG. 3. The method includes selecting a plurality of sample or base auditory signals for evaluation at 210. For example, sixty-two auditory signals may be selected for evaluation, such as by a plurality of nurses. The auditory signals may correspond to different conditions or standards, such as different IEC alarm standards for different urgency levels (e.g., low, medium and high urgency levels). The auditory signals may be, for example, IEC low, medium and high urgency alarm melodies with varying musical properties of timbre, attack and decay. Additionally, in some embodiments, different non-standard, arbitrary or random auditory signals may be selected, such as generated by a professional sound engineer.

The method 200 also includes selecting a plurality of medical messages at 211. For example, thirty medical messages may be selected, such as medical messages typically indicated using auditory signals and that are sampled from documentation of devices of interest, such as documentation for ventilators, monitors and infusion pumps. However, depending on the particular application, medical messages for different devices may be selected. In various embodiments, medical messages include messages associated with low, medium and high criticality patient conditions may be sampled, as well as device information/feedback messages, as discussed in more detail below in connection with the data chart of FIG. 4.

The auditory signals/sounds may then be played at 212. For example, the selected auditory signals/sounds may be presented to a study group for evaluation. The method 200 then includes collecting classification data at 214, such as using a data sheet on which each nurse in the study group can indicate what type of medical message they though that each auditory signal indicated. An exemplary data sheet is shown in FIG. 4. As illustrated in FIG. 4, the nurse can indicate which category of medical messages they thought each auditory signal indicated, choosing among nine categories: high criticality patient condition, rare or unexpected high criticality patient condition, reminder: high criticality alarm has been turned off, medium criticality patient condition, low criticality patient condition, equipment problem, drug or therapy delivery has started or stopped, a user action has been detected/received, and no opinion. In addition, the each nurse can indicate the particular physiological condition of a patient with which the auditory signal is associated, including, general, cardiac, artificial perfusion, ventilation, oxygen, temperature and drug/fluid delivery.

The data collected at 214 may be collected, for example, from small groups, such as groups of three to five nurses. The information for evaluation may be presented to each participant via a laptop computer on which to view, for example, the data sheet. In some embodiments, auditory signals are presented to each nurse through individual headphones. In one embodiment, all participants in a group are allowed to complete classification of a given auditory signal before the next auditory signal is presented.

With further reference to FIG. 3, the method 200 also includes performing data analysis at 216 (with one or more processors or modules) using the collected classification data to identify or select different characteristics or properties for one or more auditory device signals for medical messaging. In particular, the analysis at 216 includes in some embodiments a hierarchical cluster analysis of auditory similarities at 218. For example, in one embodiment, a 62×62 auditory signal similarity matrix may be constructed, which is coded for the number of study participants who placed each pair of auditory signals in the same top-level message category (i.e., row of the data sheet). Accordingly, this allows for the identification of clusters of auditory signals that tend to co-occur within the same message category and are, therefore, perceptually associated with that message category.

In addition, the analysis at 216 may also include in some embodiments a chi square analysis at 220. Using chi square analysis, individual auditory signals that are significantly associated with a particular message or system can be identified.

In an embodiment, the analysis at 216 also includes analyzing acoustic and musical metrics at 222. In particular, in an embodiment, mean acoustic and musical metrics are calculated within each cluster of auditory signals. Binary coding of musical properties (present or absent for each auditory signal) may be standardized before calculating the means.

Utilizing the cluster analysis of step 218, seven primary clusters associated with major categories of medical messages can be identified. In an embodiment, the seven primary clusters of auditory signals identified utilizing the method 200 of FIG. 3 are as follows: high criticality, medium criticality, low criticality, alarm reminder, equipment alert (strong), timer (strong) and information/feedback. These categories/clusters are each defined by particular acoustic and musical metrics or properties, as indicated hereinafter.

In various embodiments, the auditory alerts/alarms are defined by specific properties. The high criticality alarm cluster is defined by the following musical properties: rapidly oscillating beat pattern (not harmonious, fast tempo, repetitive (not syncopated) and complex (not simple)), staccato notes not long in duration, as well as the following acoustic properties: high Loudness (but low Articulation Index, low Sharpness and low mean frequency), high Roughness (but low Prominence Ratio).

The medium criticality alarm cluster may be defined by the following musical properties: slow (and not fast) tempo, repetitive (and not syncopated rhythm), simple (and not complex), and neither harmonious nor dissonant, as well as the following acoustic properties: lower Loudness and higher Articulation Index than high criticality alarms, low Sharpness, low mean frequency, and low Prominence Ratio.

The low criticality alarm cluster may be defined by the following musical properties: neither harmonious nor dissonant, not slow tempo, not complex, electronic timbre (not natural or unique), short (not long) and staccato notes, not low frequency, as well as the following acoustic properties: lower Loudness than medium criticality alarms, low Sharpness, low mean frequency, low Prominence Ratio, low Roughness, low Fluctuation Strength.

The alarm reminder alarm cluster may be defined by the following musical properties: dissonant (not harmonious), complex (not simple), neither slow nor fast tempo, neither repetitive nor syncopated rhythm, electronic timbre, long and staccato notes, high frequency, as well as the following acoustic properties: highest Loudness, Sharpness and mean frequency, lowest Articulation Index, lowest Prominence Ratio and highest Fluctuation Strength.

The equipment alert alarm cluster may be defined by the following musical properties: not harmonious, fast (and not slow) timbre, not natural timbre, not long notes, high (and not low frequency), as well as the following acoustic properties: same Loudness and Articulation Index as medium criticality alarm, low Sharpness, low mean frequency, high Tonality, high Prominence Ratio, low Roughness. In an embodiment, the equipment alert may indicate a low battery of a patient monitoring device.

The timer alarm cluster may be defined by the following musical properties: not dissonant (but not harmonious either), not fast tempo, not syncopated, short (and not long) notes, low frequency, as well as the following acoustic properties: Loudness equal to low criticality alarm, high Articulation Index, low Sharpness, low mean frequency, low Prominence Ratio, low tone level.

The information/feedback alarm cluster may be defined by the following musical properties: generally, a single note, neither harmonious nor dissonant, neither slow nor fast tempo, neither repetitive nor syncopated beat, not complex, not electronic timbre, not long notes, not high frequency, as well as the following acoustic properties: high Articulation Index, low Loudness, low Sharpness, low mean frequency, high tone-to-noise ratio, low tone level.

FIG. 6 is a table showing the mean values for each of the musical and acoustic properties/metrics defining each cluster or classification of alarms/messages. As illustrated therein, the dark cells indicate metric values that are distinctively large, while the white (not shaded) cells indicate metric values that are distinctively small. The lightly-shaded cells indicate metric values that are medium values (i.e., not distinctively large and not distinctively small). As will be readily appreciated, some of the numeric values for the clusters only contain large and medium values, and no small values, meaning that small values should be avoided for effective auditory signals for that particular classification of alarms/messages.

The table also indicates various patterns that help to determine the type of auditory signals that should be utilized to convey a particular alarm or message. For example, there is a pattern of decreasing Loudness with decreasing alarm criticality; Articulation Index is lowest for High criticality alarms and alarm reminders, but highest for the most benign messages of Timer and Feedback; Alarm Reminder is highest in Sharpness, Frequency and Fluctuation Strength; Equipment Alert is highest in Tonality and Prominence Ratio; Feedback is highest in Tone To Noise Ratio. In an embodiment, these unique qualities that define the auditory signals for each message type.

As indicated by the above, it has been determined that nurses perceptually differentiate among seven major types of auditory signals associated with seven distinct categories of medical messages. In addition, it has been determined that there is little differentiation among different systems or monitoring devices (such as cardiac, respiratory, general, etc.), and little differentiation between common and uncommon patient conditions.

Figure 5:
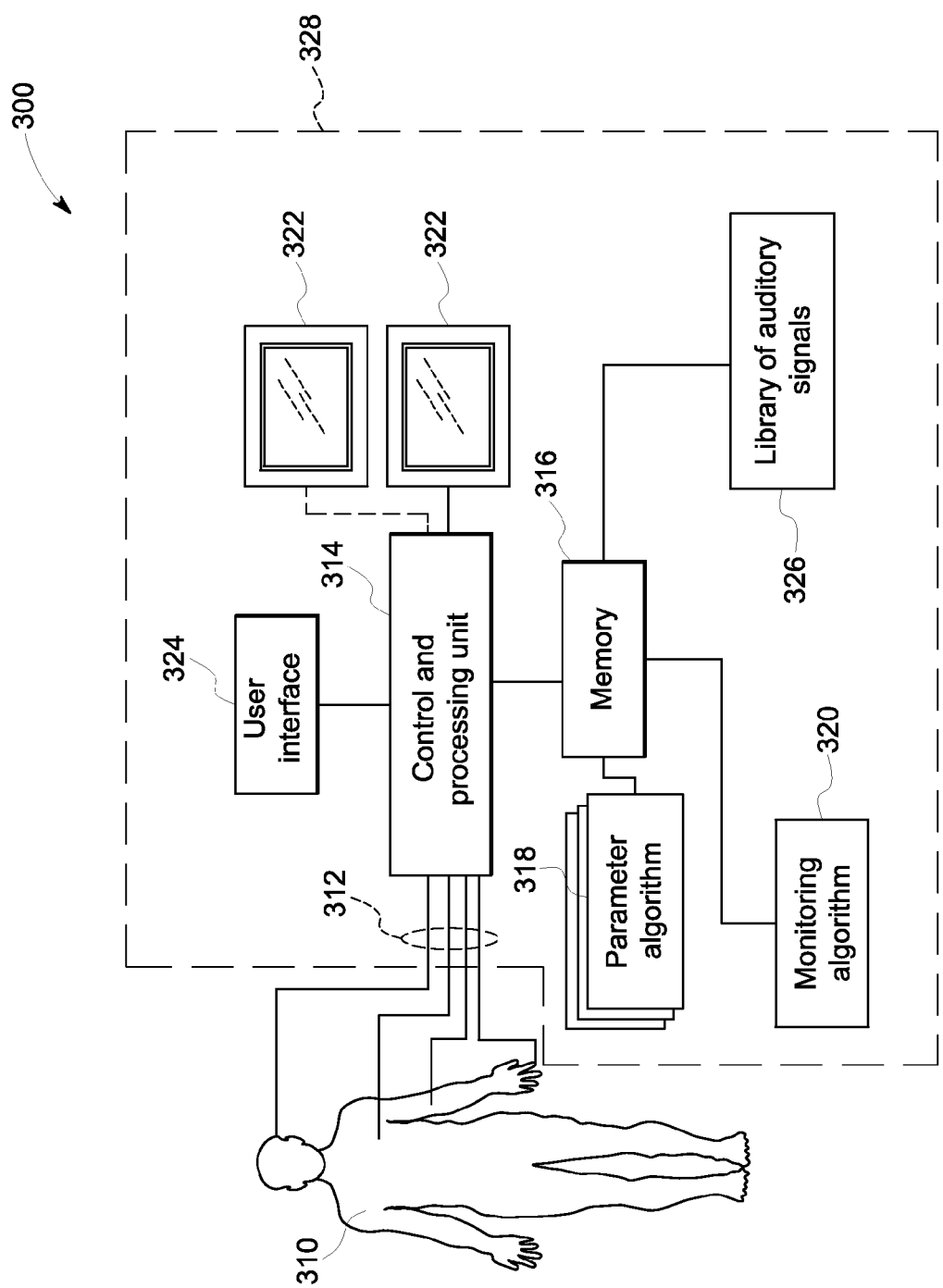
FIG. 5 is a schematic illustration of a system for physiological monitoring of a patient according to an embodiment of the present invention.

In connection with the methods of FIGS. 2 and 3, described above, an integrated library or classification structure for auditory signals that are innately associated with seven different classes of medical messages, including both alarms and information/feedback, has been derived. As also indicated above each of these seven classes of medical messages/alarms is defined by acoustic and musical properties of auditory signals. With reference to FIG. 5, this classification structure of medical messages and alarms may be integrated with a medical device connected to a patient, or with a patient monitoring system having a plurality of patient monitoring devices. By using this set of auditory signals, perceptual efficiency and discrimination may be improved, thus improving medical response and reducing alarm fatigue.

As shown in FIG. 5, in an embodiment, a patient monitoring system 300 for monitoring a subject or patient 310 is illustrated. As will be readily appreciated, the monitoring system 300 normally acquires a plurality of physiological channel signals 312 from the patient 310 via sensors (not shown), where one physiological channel signal corresponds to one measurement channel. The channel signals 312 typically comprise several types of signals, such as ECG, EEG, EMG, blood pressure, respiration, pulse, temperature and plethysmographic signals.

Based on the raw real-time physiological signal data obtained from the subject 14, a plurality of physiological parameters may be derived, each physiological parameter being calculated from the waveform data of one or more of the physiological channel signals acquired from the subject. If a physiological parameter is derived from more than one physiological channel signal, i.e. from more than one measurement channel, the said channel signals are usually of the same signal type. The physiological parameter may thus also represent a waveform signal value determined over a predefined period of time, although the physiological parameter is typically a distinct parameter derived from one or more measurement channels, such as heart rate derived from one or more ECG channel signals or a $SpO_2$ value derived from one or more plethysmographic channel signals. In an embodiment, the physiological parameters may include heart rate, heart rate variability, ST segment measurements, respiration rate, pulse rate, oxygen saturation, systolic, diastolic and/or mean blood pressure, entropy, sedation and the like.

The physiological channel signals 312 acquired from the subject 310 are supplied to a control and processing unit 314 through a pre-processing stage (not shown) comprising typically an input amplifier and a filter, for example. The control and processing unit 314 converts the signals into digitized format for each measurement channel. The digitized signal data may then be stored in the memory 316 of the control and processing unit 314. In an embodiment, the digitized signal data is utilized by parameter algorithms 318 adapted to record, when executed by the control and processing unit 314, the time series of the physiological parameters to be monitored. The obtained time series of the physiological parameters may be stored in the memory 316. Moreover, the parameter algorithms 318 of the control and processing unit 314 process the digitized signal data and measurements to identify past, current or future occurrence of physiological events.

Generally, each physiological parameter may be assigned one or more alarm limits to alert the nursing staff when the parameter reaches or crosses the alarm limit. For example, a physiological parameter, such as heart rate, may be assigned multiple alarm levels of increasing priority/severity and alarm escalation may be used to escalate a low level alarm to the next level of priority/severity, if the low level alarm persists and/or goes unacknowledged long enough. In an embodiment, the control and processing unit 314 includes an alarm generator for notifying a clinical user with an appropriate alarm signal when a monitored parameter reaches or exceeds the preset alarm limit for such parameter, as discussed in detail hereinafter.

In particular, in an embodiment, the control and processing unit 314 uses a signal monitoring algorithm 320 to monitor the successive values of the parameter and to detect events and to generate alarms based on the parameter values. This typically involves comparison of the parameter values with at least one alarm limit stored in memory 316 to detect whether an alarm is to be raised. When a crossing of an alarm limit is detected, the control and processing unit 314 may inform the clinician of the alarm.

The control and processing unit 314 is further configured to control the display unit(s) 322 of the system. Interaction with users of the apparatus/system may occur through user interface 324.

With further reference to FIG. 5, the control and processing unit 314 includes an integrated library or classification structure 326 of auditory signals stored in memory 316 that may be referenced when a monitored parameter reaches or exceeds a preset alarm limit for such parameter or when other medical messages must be communicated to a user. In operation, the control and processing unit 314 is configured to operate a speaker (not shown) of the system 300 to enable the speaker to output an audible indication, which may be referred to as an audible message, such as an audible medical message, for example, an auditory alarm or warning. In particular, upon detection of a physiological parameter, and determining that the parameter value excesses a threshold value stored in memory 316, the control and processing unit 314 selects an auditory alarm or alert from the library 326 and generates the alarm to alert nurses or physicians to the patient's condition. In an embodiment, as discussed above, the library 326 may contain a plurality of auditory signals that are separated into seven categories of alarms: a high criticality alarm, a medium criticality alarm, a low criticality alarm, an alarm disabled alert/reminder, an equipment alert, a timer, and an information/feedback alert. Each category of alarms is defined by the musical and acoustic properties discussed above in connection with FIGS. 1-4.

In an embodiment, the control and processing unit 314, memory 316, parameter algorithm 318, monitoring algorithm 320, the display devices 322, the user interface 324 and the library of auditory signals 326 may be embodied in a single monitoring device, such as monitoring device 328, that is configured to monitor one or more physiological parameters of a patient. In other embodiments, the system 300 may include a plurality of monitoring devices that provide data regarding the monitored physiological parameters of a patient to a central control and processing unit, whereby the central control and processing unit is configured to generate auditory signals in dependence upon the various monitored parameters and preset message or alert threshold levels.

In various embodiments, the audible indication is designed and/or generated based on different criteria, such as different acoustical and/or musical properties that convey a specific semantic character as described herein. In general, a set of medical messages or audible indications that are desired to be broadcast to a clinician may be determined, for example, initially selected. In one embodiment, the audible indications may be used to inform listeners that a particular medical condition exists and/or to inform the clinician that some action potentially needs to be performed. Thus, each audible indication may include different elements or acoustical properties, as discussed above. For example, acoustical properties may communicate the medical condition (or patient status) to the clinician. For example, how the audible indication/message is broadcast, and the tone, frequency, and/or timbre of the audible indication may provide information regarding the severity of the alarm or warning, such as that a patient's heart is stopped, breathing has ceased, the imaging table is moving, etc.

In particular, various embodiments provide a conceptual framework and a perceptual framework for defining audible indications or messages. In some embodiments, sound profiles for medical images are defined that are used to generate the audible indications, as discussed above. The sound profiles map different audible messages to sounds corresponding to the audible indications, such as to indicate a particular condition or operation. For example, correlations between variables and perceptions as described herein may be used to define one or more auditory sounds.

As will be readily appreciated, current medical alarm standards focus on communicating patient conditions of various levels of criticality. Separate standards define auditory signals for non-alarm conditions. However, there is no one standard that specifies and differentiates the full set of medical messages that may be communicated with auditory signals. Indeed, there is no integrated standard that takes into account differentiation between alarms and non-alarm messages as well as cognitive specificity to the various types of messages. In essence, there is no relative accounting of similarities and differences in acoustic and musical properties of auditory signals that communicate different types of medical messages.

Accordingly, the system and method of the present invention therefore provides an integrated library of auditory signals that specify and differentiate among seven major types of medical messages based upon perceptual properties that are innately salient to nurses. In connection with this, the auditory signals associated with high criticality patient conditions are unique and are more highly associated with high criticality alarm conditions than currently used melodies. Moreover, the different message categories defined by the present invention define an integrated whole that includes both alarms and medical device messages. In particular, the present invention simultaneously examines acoustic and musical properties of auditory device signals associated with meaningful categories of medical messages that span the entire message space.

In an embodiment, a system is provided. The system includes at least one device configured to generate a plurality of messages and a control unit in the at least one medical device. The control unit is configured to generate an auditory signal corresponding to one of the plurality of messages, wherein the auditory signal is configured based on a functional relationship linking psychological sound perceptions in a clinical environment to acoustic and musical sound properties. The functional relationship includes a plurality of types of auditory messages defining seven unique categories. In an embodiment, the seven auditory message categories include high criticality, medium criticality, low criticality, reminder, equipment alert, timer, and information/feedback. In an embodiment, the high criticality auditory message category encompasses auditory signals having musical properties including a rapidly oscillating beat pattern, not harmonious, fast tempo, repetitive (not syncopated), complex (not simple), staccato notes not long in duration, and having acoustic properties including high Loudness, low Articulation Index, low Sharpness and low mean frequency, high Roughness and low Prominence Ratio. In an embodiment, the medium criticality auditory message category encompasses auditory signals having musical properties including slow (and not fast) tempo, repetitive (and not syncopated rhythm), simple (and not complex), and neither harmonious nor dissonant, and having acoustic properties including lower Loudness and higher Articulation Index than high criticality auditory signals, low Sharpness, low mean frequency, and low Prominence Ratio. In an embodiment, the low criticality auditory message category encompasses auditory signals having musical properties including neither harmonious nor dissonant, not slow tempo, not complex, electronic timbre (not natural or unique), short (not long) and staccato notes, not low frequency, and having acoustic properties including lower Loudness than medium criticality alarms, low Sharpness, low mean frequency, low Prominence Ratio, low Roughness and low Fluctuation Strength. In an embodiment, the reminder auditory message category encompasses auditory signals having musical properties including dissonant (not harmonious), complex (not simple), neither slow nor fast tempo, neither repetitive nor syncopated rhythm, electronic timbre, long and staccato notes, high frequency, and having acoustic properties including high Loudness, Sharpness and mean frequency, low Articulation Index, low Prominence Ratio and high Fluctuation Strength. In an embodiment, the equipment alert auditory message category encompasses auditory signals having musical properties including not harmonious, fast (and not slow) timbre, not natural timbre, not long notes, high (and not low) frequency, and having acoustic properties including a same Loudness and Articulation Index as medium criticality auditory signals, low Sharpness, low mean frequency, high Tonality, high Prominence Ratio and low Roughness. In an embodiment, the timer auditory message category encompasses auditory signals having musical properties including not dissonant, not harmonious, not fast tempo, not syncopated, short (and not long) notes, low frequency, and having acoustic properties including Loudness equal to low criticality auditory signals, high Articulation Index, low Sharpness, low mean frequency, low Prominence Ratio and low tone level. In an embodiment, the information/feedback message category encompasses auditory signals having musical properties including approximately a single note, neither harmonious nor dissonant, neither slow nor fast tempo, neither repetitive nor syncopated beat, not complex, not electronic timbre, not long notes, not high frequency, and having acoustic properties including high Articulation Index, low Loudness, low Sharpness, low mean frequency, high tone-to-noise ratio and low tone level.

In an embodiment, a method for providing auditory messages for a physiological monitoring device is provided. The method includes the steps of defining a plurality of auditory states representing a plurality of different medical messages or conditions, detecting one or more medical evens and correlating the medical event to one of the medical messages or conditions, and generating an auditory message corresponding to the detected medical event, and outputting audibly the auditory message corresponding to the detected medical event. The auditory message is configured based on a functional relationship linking psychological sound perceptions in a clinical environment to acoustic and musical sound variables, and the functional relationship includes a plurality of types of auditory messages defining seven unique categories. In an embodiment, the seven auditory message categories include high criticality, medium criticality, low criticality, reminder, equipment alert, timer, and information/feedback. In an embodiment, the high criticality auditory message category encompasses auditory signals having musical properties including a rapidly oscillating beat pattern, not harmonious, fast tempo, repetitive (not syncopated), complex (not simple), staccato notes not long in duration, and having acoustic properties including high Loudness, low Articulation Index, low Sharpness and low mean frequency, high Roughness and low Prominence Ratio. In an embodiment, the medium criticality auditory message category encompasses auditory signals having musical properties including slow (and not fast) tempo, repetitive (and not syncopated rhythm), simple (and not complex), and neither harmonious nor dissonant, and having acoustic properties including lower Loudness and higher Articulation Index than high criticality auditory signals, low Sharpness, low mean frequency, and low Prominence Ratio. In an embodiment, the low criticality auditory message category encompasses auditory signals having musical properties including neither harmonious nor dissonant, not slow tempo, not complex, electronic timbre (not natural or unique), short (not long) and staccato notes, not low frequency, and having acoustic properties including lower Loudness than medium criticality alarms, low Sharpness, low mean frequency, low Prominence Ratio, low Roughness and low Fluctuation Strength. In an embodiment, the reminder auditory message category encompasses auditory signals having musical properties including dissonant (not harmonious), complex (not simple), neither slow nor fast tempo, neither repetitive nor syncopated rhythm, electronic timbre, long and staccato notes, high frequency, and having acoustic properties including high Loudness, Sharpness and mean frequency, low Articulation Index, low Prominence Ratio and high Fluctuation Strength. In an embodiment, the equipment alert auditory message category encompasses auditory signals having musical properties including not harmonious, fast (and not slow) timbre, not natural timbre, not long notes, high (and not low) frequency, and having acoustic properties including a same Loudness and Articulation Index as medium criticality auditory signals, low Sharpness, low mean frequency, high Tonality, high Prominence Ratio and low Roughness. In an embodiment, the timer auditory message category encompasses auditory signals having musical properties including not dissonant, not harmonious, not fast tempo, not syncopated, short (and not long) notes, low frequency, and having acoustic properties including Loudness equal to low criticality auditory signals, high Articulation Index, low Sharpness, low mean frequency, low Prominence Ratio and low tone level. In an embodiment, the information/feedback message category encompasses auditory signals having musical properties including approximately a single note, neither harmonious nor dissonant, neither slow nor fast tempo, neither repetitive nor syncopated beat, not complex, not electronic timbre, not long notes, not high frequency, and having acoustic properties including high Articulation Index, low Loudness, low Sharpness, low mean frequency, high tone-to-noise ratio and low tone level. In an embodiment, the step of generating an auditory message includes retrieving the auditory message from one of the seven unique categories of auditory messages arranged in a library of auditory messages stored in a database of the monitoring device.

In an embodiment, a system is provided. The system includes a device configured to monitor at least one physiological parameter of a patient, a control unit, and a database associated with the control unit. The database includes a classification structure for auditory medical messages, wherein the classification structure includes seven categories of auditory medical messages. Upon detection of a physiological patient parameter having a value exceeding a threshold value, the control unit is configured to select an auditory signal from one of the seven categories and audibly output the auditory signal. In an embodiment, the seven categories of auditory medical messages include high criticality alerts, medium criticality alerts, low criticality alerts, reminder alerts, equipment alerts, timer alerts, and information/feedback alerts.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope.

While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. §122, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A system, comprising:
   at least one device configured to generate a plurality of messages;
   a control unit in the at least one medical device configured to generate an auditory signal corresponding to one of the plurality of messages, wherein the auditory signal is configured based on a functional relationship linking psychological sound perceptions in a clinical environment to acoustic and musical sound properties; and
   wherein the functional relationship includes a plurality of types of auditory messages defining seven unique categories that are generated by common semantic experiences of healthcare providers in a medical environment, and
   the seven auditory message categories include high criticality, medium criticality, low criticality, reminder, equipment alert, timer, and information/feedback.

2. The system of claim 1, wherein:
   the high criticality auditory message category encompasses auditory signals having musical properties including a rapidly oscillating beat pattern, not harmonious, fast tempo, repetitive (not syncopated), complex (not simple), staccato notes not long in duration, and having acoustic properties including high Loudness, low Articulation Index, low Sharpness and low mean frequency, high Roughness and low Prominence Ratio.

3. The system of claim 2, wherein:
   the medium criticality auditory message category encompasses auditory signals having musical properties including slow (and not fast) tempo, repetitive (and not syncopated rhythm), simple (and not complex), and neither harmonious nor dissonant, and having acoustic properties including lower Loudness and higher Articulation Index than high criticality auditory signals, low Sharpness, low mean frequency, and low Prominence Ratio.

4. The system of claim 3, wherein:
   the low criticality auditory message category encompasses auditory signals having musical properties including neither harmonious nor dissonant, not slow tempo, not complex, electronic timbre (not natural or unique), short (not long) and staccato notes, not low frequency, and having acoustic properties including lower Loudness than medium criticality alarms, low Sharpness, low mean frequency, low Prominence Ratio, low Roughness and low Fluctuation Strength.

5. The system of claim 4, wherein:
   the reminder auditory message category encompasses auditory signals having musical properties including dissonant (not harmonious), complex (not simple), neither slow nor fast tempo, neither repetitive nor syncopated rhythm, electronic timbre, long and staccato notes, high frequency, and having acoustic properties including high Loudness, Sharpness and mean frequency, low Articulation Index, low Prominence Ratio and high Fluctuation Strength.

6. The system of claim 5, wherein:
   the equipment alert auditory message category encompasses auditory signals having musical properties including not harmonious, fast (and not slow) timbre, not natural timbre, not long notes, high (and not low) frequency, and having acoustic properties including a same Loudness and Articulation Index as medium criticality auditory signals, low Sharpness, low mean frequency, high Tonality, high Prominence Ratio and low Roughness.

7. The system of claim 6, wherein:
   the timer auditory message category encompasses auditory signals having musical properties including not dissonant, not harmonious, not fast tempo, not syncopated, short (and not long) notes, low frequency, and having acoustic properties including Loudness equal to low criticality auditory signals, high Articulation Index, low Sharpness, low mean frequency, low Prominence Ratio and low tone level.

8. The system of claim 7, wherein:
   the information/feedback message category encompasses auditory signals having musical properties including approximately a single note, neither harmonious nor dissonant, neither slow nor fast tempo, neither repetitive nor syncopated beat, not complex, not electronic timbre, not long notes, not high frequency, and having acoustic properties including high Articulation Index, low Loudness, low Sharpness, low mean frequency, high tone-to-noise ratio and low tone level.

9. A method for providing auditory messages for a physiological monitoring device, comprising the steps of:
   defining a plurality of auditory states representing a plurality of different medical messages or conditions;

detecting one or more medical evens and correlating the medical event to one of the medical messages or conditions;

generating an auditory message corresponding to the detected medical event, wherein the auditory message is configured based on a functional relationship linking psychological sound perceptions in a clinical environment to acoustic and musical sound variables;

outputting audibly the auditory message corresponding to the detected medical event; and wherein the functional relationship includes a plurality of types of auditory messages defining seven unique categories that are generated by common semantic experiences of healthcare providers in a medical environment, and the seven auditory message categories include high criticality, medium criticality, low criticality, reminder, equipment alert, timer, and information/feedback.

10. The method according to claim 9, wherein:

the high criticality auditory message category encompasses auditory signals having musical properties including a rapidly oscillating beat pattern, not harmonious, fast tempo, repetitive (not syncopated), complex (not simple), staccato notes not long in duration, and having acoustic properties including high Loudness, low Articulation Index, low Sharpness and low mean frequency, high Roughness and low Prominence Ratio.

11. The method according to claim 10, wherein:

the medium criticality auditory message category encompasses auditory signals having musical properties including slow (and not fast) tempo, repetitive (and not syncopated rhythm), simple (and not complex), and neither harmonious nor dissonant, and having acoustic properties including lower Loudness and higher Articulation Index than high criticality auditory signals, low Sharpness, low mean frequency, and low Prominence Ratio.

12. The method according to claim 11, wherein:

the low criticality auditory message category encompasses auditory signals having musical properties including neither harmonious nor dissonant, not slow tempo, not complex, electronic timbre (not natural or unique), short (not long) and staccato notes, not low frequency, and having acoustic properties including lower Loudness than medium criticality alarms, low Sharpness, low mean frequency, low Prominence Ratio, low Roughness and low Fluctuation Strength.

13. The method according to claim 12, wherein:

the reminder auditory message category encompasses auditory signals having musical properties including dissonant (not harmonious), complex (not simple), neither slow nor fast tempo, neither repetitive nor syncopated rhythm, electronic timbre, long and staccato notes, high frequency, and having acoustic properties including high Loudness, Sharpness and mean frequency, low Articulation Index, low Prominence Ratio and high Fluctuation Strength.

14. The method according to claim 13, wherein:

the equipment alert auditory message category encompasses auditory signals having musical properties including not harmonious, fast (and not slow) timbre, not natural timbre, not long notes, high (and not low) frequency, and having acoustic properties including a same Loudness and Articulation Index as medium criticality auditory signals, low Sharpness, low mean frequency, high Tonality, high Prominence Ratio and low Roughness.

15. The method according to claim 14, wherein:

the timer auditory message category encompasses auditory signals having musical properties including not dissonant, not harmonious, not fast tempo, not syncopated, short (and not long) notes, low frequency, and having acoustic properties including Loudness equal to low criticality auditory signals, high Articulation Index, low Sharpness, low mean frequency, low Prominence Ratio and low tone level.

16. The method according to claim 15, wherein:

the information/feedback message category encompasses auditory signals having musical properties including approximately a single note, neither harmonious nor dissonant, neither slow nor fast tempo, neither repetitive nor syncopated beat, not complex, not electronic timbre, not long notes, not high frequency, and having acoustic properties including high Articulation Index, low Loudness, low Sharpness, low mean frequency, high tone-to-noise ratio and low tone level.

17. The method according to claim 16, wherein:

the step of generating an auditory message includes retrieving the auditory message from one of the seven unique categories of auditory messages arranged in a library of auditory messages stored in a database of the monitoring device.

18. A system, comprising:

a device configured to monitor at least one physiological parameter of a patient;

a control unit; and a database associated with the control unit, the database including a classification structure for auditory medical messages, the classification structure including seven categories of auditory medical messages that are generated by common semantic experiences of healthcare providers in a medical environment; and wherein upon detection of a physiological patient parameter having a value exceeding a threshold value, the control unit is configured to select an auditory signal from one of the seven categories and audibly output the auditory signal, and the seven categories of auditory medical messages include high criticality alerts, medium criticality alerts, low criticality alerts, reminder alerts, equipment alerts, timer alerts, and information/feedback alerts.

* * * * *